(12) United States Patent
Witte et al.

(10) Patent No.: US 6,611,721 B1
(45) Date of Patent: Aug. 26, 2003

(54) BREAK-AWAY EXTRACTABLE LEAD

(75) Inventors: Joachim Witte, Berlin (DE); Max Schaldach, Erlangen (DE); Sven Poga, Münster (DE)

(73) Assignee: Biotronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/603,823

(22) Filed: Jun. 26, 2000

(30) Foreign Application Priority Data

Jun. 25, 1999 (DE) .......................... 199 30 237

(51) Int. Cl.$^7$ ................................. A61N 1/05
(52) U.S. Cl. ......................................... 607/126
(58) Field of Search ................. 607/115, 116, 607/119, 122, 126, 128; 600/372–375, 377, 381; 606/129

(56) References Cited

U.S. PATENT DOCUMENTS

| | | |
|---|---|---|
| 4,236,529 A | 12/1980 | Little ........................... 128/785 |
| 4,262,678 A | 4/1981 | Stokes .......................... 128/786 |
| 4,506,679 A | 3/1985 | Mann ........................... 128/785 |
| 4,841,971 A | 6/1989 | Hess ......................... 128/419 P |
| 4,954,922 A | 9/1990 | Gaus et al. ..................... 361/42 |
| 5,374,286 A | * 12/1994 | Morris ......................... 600/375 |
| 5,383,924 A | * 1/1995 | Brehier ......................... 607/126 |
| 5,807,399 A | * 9/1998 | Laske et al. ................. 606/108 |
| 5,876,408 A | 3/1999 | Alt et al. |
| 5,908,447 A | * 6/1999 | Schroeppel et al. ........ 607/126 |

FOREIGN PATENT DOCUMENTS

| | | | |
|---|---|---|---|
| DE | 30 20 586 | 12/1981 | |
| DE | 30 20 586 A1 | 12/1981 | |
| DE | 3020586 | * 12/1981 | ............. A61N/1/04 |
| EP | 0 408 358 A2 | 1/1991 | |
| WO | WO 98/20933 | * 5/1998 | ................. 607/126 |

OTHER PUBLICATIONS

Albrecht Urbaszek, "Elektrostimulation des Herzens", Fachverlagn Schiele & Schon GmbH. 1996.

* cited by examiner

*Primary Examiner*—Kennedy Schaetzle
*Assistant Examiner*—Kristen Droesch
(74) *Attorney, Agent, or Firm*—Venable LLP; Robert Kinberg; Chad C. Anderson

(57) ABSTRACT

An electrode arrangement is provided having an electrode line which has a closed casing for sealing off its interior relative to the surrounding area. At its distal end, electrically conducting surface regions serve as electrodes. A fixing mechanism anchors the distal end in a body tissue, in particular heart tissue and is adapted to be separable from the rest of the electrode line in such a way that the rest of the electrode line is also closed at its distal end when the fixing mechanism is separated off. The interior of the electrode line is sealed off relative to the surrounding area even when the fixing element is separated off. The electrode arrangement is characterized by a mechanism for separating off the fixing mechanism, which is adapted to effect separation by virtue of forces acting axially within the electrode line.

10 Claims, 5 Drawing Sheets

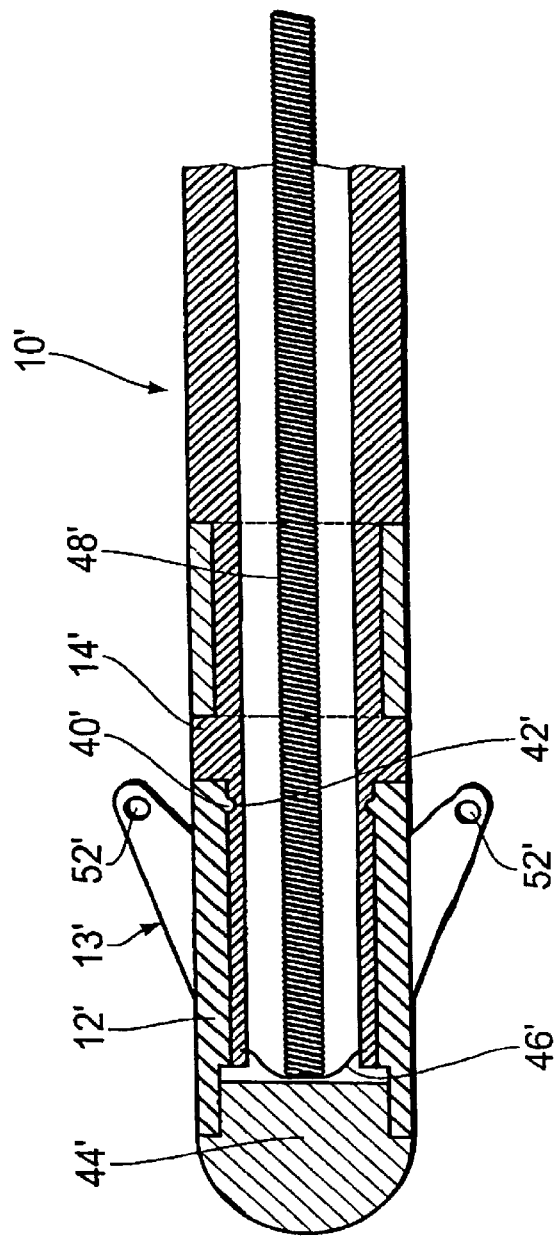
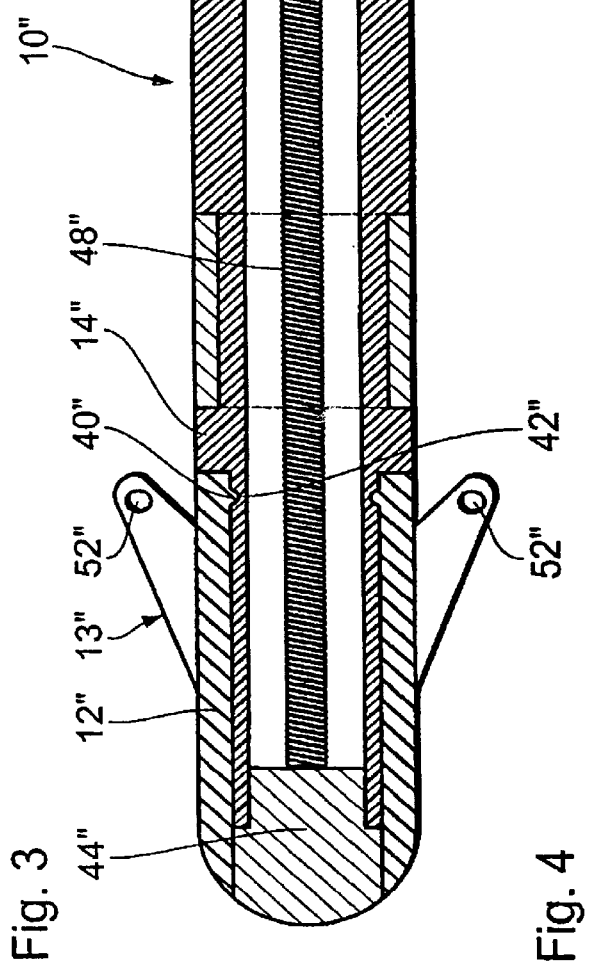
Fig. 3
Fig. 4

BREAK-AWAY EXTRACTABLE LEAD

BACKGROUND OF THE INVENTION

The invention concerns an electrode arrangement having an electrode line which has a closed casing for sealing off its interior relative to the surrounding area and, at its distal end, an electrically conducting surface regions serving as electrodes, as well as fixing means for anchoring the distal end in a body tissue, in particular heart tissue, wherein the fixing means are adapted to be separable from the rest of the electrode line in such a way that the rest of the electrode line is also closed at its distal end when the fixing means are separated off so that the interior of the electrode line is sealed off relative to the surrounding area even when the fixing element is separated off.

Electrode arrangements of this kind are known, for example from DE 30 20 586. Besides the specified electrode arrangements with tines, small barb-like prongs at the outermost distal end of the electrode line, electrode lines with screwing-in tips are also known. The described fixing means serve to anchor the distal end of the electrode line in the cardiac tissue in order to hold it in a defined position and to maintain constant stimulation conditions as far as possible.

An electrode line is introduced, for example, by way of a vein into an atrium or a ventricle of a human heart. In some cases, an electrode line has to be removed again. This gives rise to problems in which the electrode line is anchored in the cardiac tissue, the myocardium, by means of the described fixing means, because the fixing means grows into the tissue as time passes. This makes it more difficult to remove the cardiac pacemaker electrodes, for example, for the purposes of replacement thereof.

Therefore, electrode lines with fixing means that can be separated off have been proposed, and can be found in U.S. Pat. Nos. 5,383,924, 5,908,447, and above-mentioned DE 30 20 586.

An indication in regard to the removal of an electrode line is afforded when infection has been found to occur in the region of a pacemaker connected to the electrode line or in the region of the electrode line itself. In such situations removal of the electrode line should as far as possible not contribute to spreading the infection. The known electrode lines leave something to be desired in this respect.

Furthermore, after some years, not only do the fixing means grow into the myocardium but the electrode line itself is also enclosed by tissue, for example, where it bears against a vessel wall, for example the vena cava. In such situations, removal of the electrode line should entail a minimum amount of injury and damage to the enclosing tissue.

SUMMARY OF THE INVENTION

The object of the invention is to provide an electrode arrangement which is simple to remove and without unnecessary health risks.

In accordance with the invention, this object is attained with an electrode arrangement of the kind set forth herein, which has means for separating off the fixing means adapted to effect separation of the fixing means by virtue of forces acting axially within the electrode line.

The invention is based on the notion of avoiding stresses on the patient which occur due to avoidable movements in the region of the outer casing of the electrode line. Avoidable movements of that kind are, for example, rotation of the electrode line as disclosed in DE 30 20 586 about its longitudinal axis in order to unscrew the electrode line from the fixing means described therein. The aim is also to avoid such loadings which are due to a separating device which is to be pushed over the electrode line, as are described in U.S. Pat. No. 5,383,924. Finally, the aim is to avoid the health risks which arise due to an electrode line which is open at the distal end after separation of the fixing means, as septic fluids in the interior of the electrode line can issue from that open end thereof. Those considerations finally led to the realization that electrode lines which are to be separated from the fixing means solely by longitudinal forces acting in the electrode line satisfy all demands. This concept of the invention embraces two variants of the invention, namely one variant in which purely passive separation of the fixing means from the rest of the electrode line is effected solely by pulling on the electrode line, and another variant in which the separation of fixing means and electrode line is actively implemented or promoted by means which are provided in the electrode line.

An advantageous feature of the electrode line according to the invention provides that after separation from the fixing means the electrode line is of a uniform diameter over its entire length or tapers towards the distal end. That makes it easier to withdraw the electrode lines if they should be enclosed by tissue at any point.

Preferably, the fixing means are connected to the rest of the electrode by way of a desired-separation location in such a way that the connection is separable in the region of the desired-separation location by defined forces which are predetermined by the configuration of the desired-separation location. The definedly predetermined forces cause the fixing means to be released from the rest of the electrode line, preferably under the influence of such forces as can be exerted by the cardiac tissue as a reaction to tensile forces exerted on the electrode in the longitudinal direction of the electrode line. The forces required for separation of the desired-separation location depend on the construction thereof. Influencing parameters in this respect are the geometry of the connection and the nature of the material used. By virtue of variations in those influencing parameters, it is possible for one skilled in the art to design the desired-separation location in such a way that forces which are to be exerted by the cardiac tissue itself are sufficient to separate the fixing means from the remainder of the electrode line. Such a design configuration in respect of the desired-separation location makes it possible on the one hand for the end of the electrode line to be securely anchored and on the other hand for the electrode line to be removed for replacement purposes without damaging the cardiac tissue.

In a prembodiment, the fixing means or the electrode line have a projection in the region of the desired-separation location, which engages into a corresponding recess in the respective other part. Such a latching arrangement for the desired-separation location can easily be designed in such a way that it separates under the influence of defined forces.

An alternative embodiment is distinguished by a releasable mechanical coupling between the fixing means and the rest of the electrode line. An actuating means is brought into engagement with the coupling to release the coupling. In contrast to the above-described alternative embodiment in which the desired-separation location separates passively as a reaction to the influence of defined forces, the connection between the fixing means and the rest of the electrode line, in the case of the last-mentioned alternative embodiment, can be released actively by means of the corresponding actuating means. The advantage of the last-mentioned alternative embodiment is that the forces which act upon replacement of an electrode line in the myocardium can be even less. On the other hand, the higher level of structural expenditure for the electrode line is a counterpart consideration.

In a preferred configuration of the last-mentioned alternative embodiment, the coupling has retaining or detent elements which engage behind a projection on the fixing means and which are to be moved by the actuating means into a position of releasing the projection. A coupling of this nature can be easily constructed with a small number of components, in such a way that it is reliable in operation. A detailed description of such a coupling is to be found herein.

In the case of an electrode arrangement with an electrically conducting surface at its distal end, to serve as a tip electrode, the desired-separation location in a preferred embodiment is of such a nature that the fixing means can be separated from the rest of the electrode line in such a way that upon separation the tip electrode remains on the electrode line.

An alternative is distinguished in that the electrode line has electrical contact elements for contacting the tip electrode, so that the fixing means are separable from the rest of the electrode line in such a way that, upon separation, the tip electrode remains on the fixing means.

The fixing means preferably has marking means which can be located by electromagnetic or acoustic locating means, such as for example an X-ray machine. Such marking means make it possible to locate a fixing means which has remained in the myocardium after the removal of an electrode line and to position an electrode line which is to be re-introduced, so that the fixing means thereof do not penetrate into the cardiac tissue at the same location as the preceding electrode line.

If the fixing means are such tines which are of a barb-like configuration, the marking means are preferably disposed in the tines.

Furthermore, a preferred electrode arrangement is one which is characterized by a synthetic resin material in the region of the desired-separation location, said material being plastic upon connection of the fixing means to the rest of the electrode line. The plastic synthetic resin material preferably contains silicone. The synthetic resin material can selectively or simultaneously perform a sealing and adhesion, that is to say gluing, function. As it is plastic or fluid when the fixing means are connected to the rest of the electrode line, it is suitable for completely filling all gaps which could remain between the fixing means and the rest of the electrode line.

It is to be noted that the features of the invention can also be transferred to those electrode arrangements which, instead of fixing means with so-called tines, have for example screwing-in tips of a corkscrew-type configuration as fixing means and possibly additionally as the electrode. Screwing-in tips of that kind can also be connected to the rest of the electrode line in the manner described hereinbefore and also as described in the specific description.

BRIEF DESCRIPTION OF THE DRAWINGS

The invention will now be described in greater detail by means of embodiments with reference to the drawings in which:

FIG. 3 shows an alternative embodiment of a distal end of an electrode line with fixing means which can be passively separated off, and FIG. 4 shows a further alternative embodiment of the distal end of an electrode line with separable fixing means.

DETAILED DESCRIPTION OF THE INVENTION

Figure 1A:
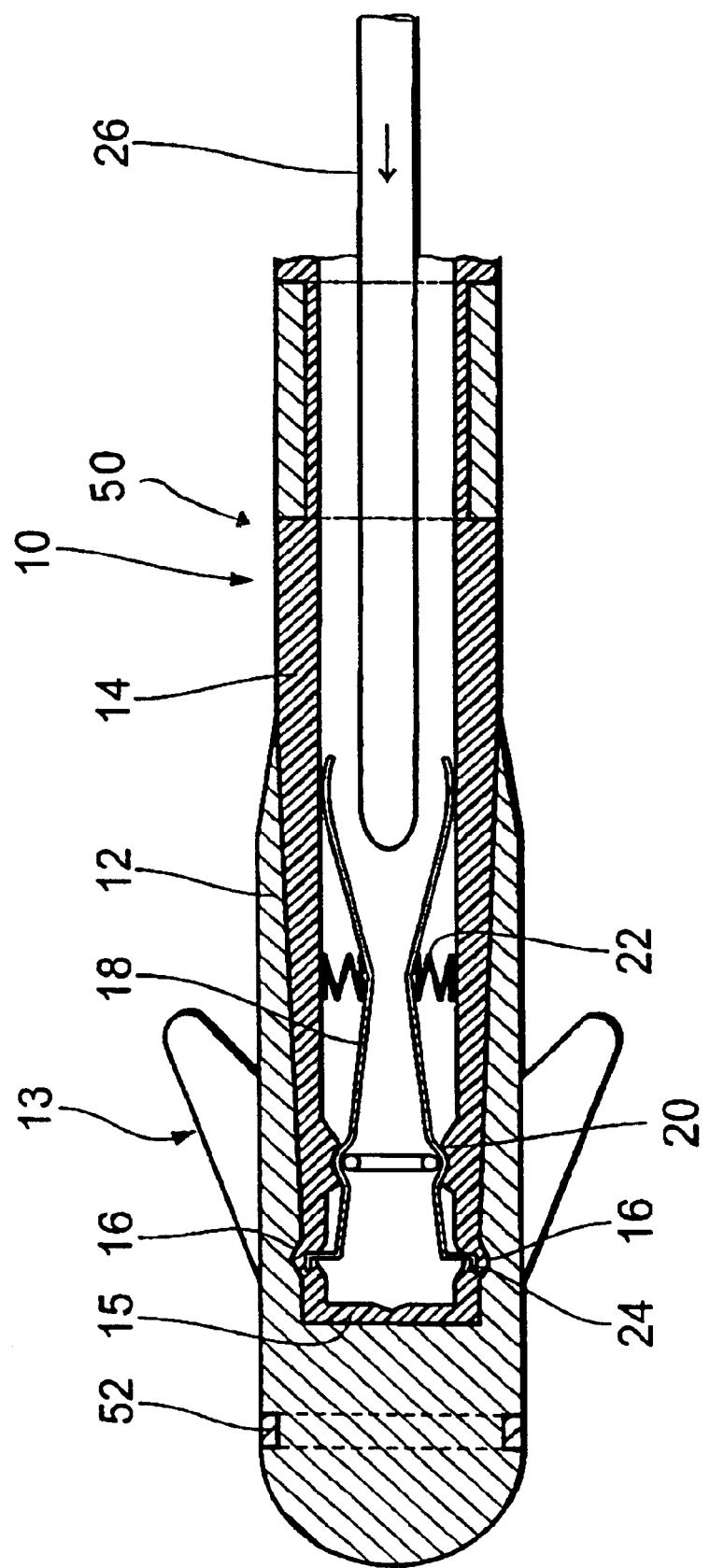
FIGS. 1a to c show the distal end of an electrode line with fixing means which can be actively separated off.
Figure 1B:
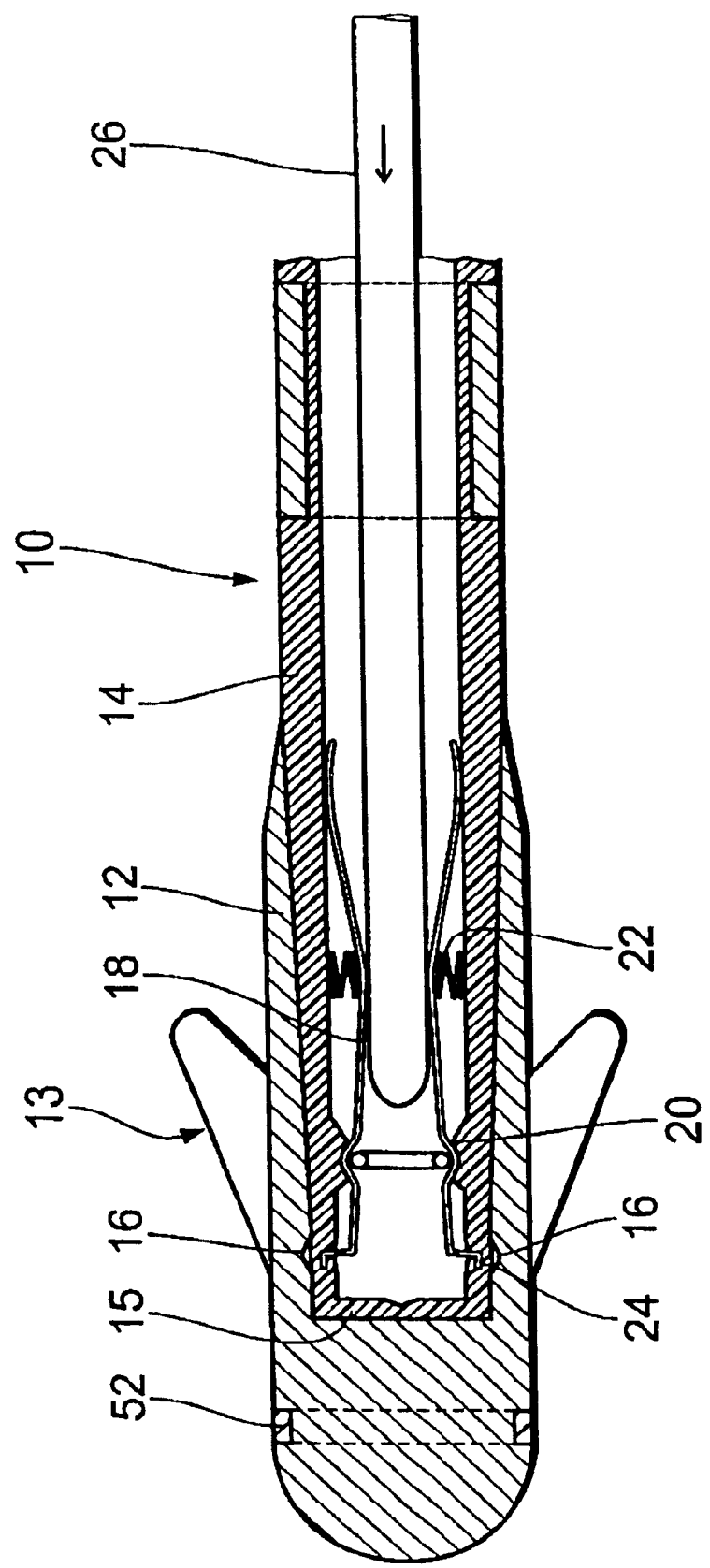

The distal end of an electrode line 10, which is shown in FIG. 1, has fixing means 12 with barb-like tines 13 of silicone synthetic resin. The electrode line has a casing 14 which is closed therearound and which seals off the interior of the electrode line with respect to the area surrounding same. The casing 14 has a closed end wall 15 at its distal end. The fixing means 12 forms a cap at the end of the electrode line 10 and is connected to the casing 14 thereof by way of a mechanical coupling formed on the part of the casing 14 by projections 16 engaging into corresponding recesses in the fixing means 12. The casing 14 is urged outwardly in the region of the projections 16 by spring bars 18 which are mounted pivotably at 20. Compression springs 22 support the pressure of the spring bars 18, which is directed outwardly at the distal ends 24 thereof, but the compression springs 22 are not absolutely necessary by virtue of the configuration of the spring bars 18. The function of the compression springs 22 can also be implemented solely by the leaf springs which are formed integrally on the spring bars 18. At their distal ends 24, the spring bars 18 are connected to the casing 14, more specifically in the region of the projections 16.

A bar 26 serves to release the mechanical coupling. The bar 26 passes between the spring bars 18 by longitudinal displacement of the bar 26 in the direction indicated by the arrow in FIG. 1, and urges the spring bars 18 away from each other at their end adjacent the bar 26, against the spring biasing effect, so that the bent-away detent ends 24 of the spring bars 18 retract the projections 16 in the casing 14 inwardly out of the corresponding recesses in the fixing means 12 and release them; see FIG. 1b.

Figure 1C:
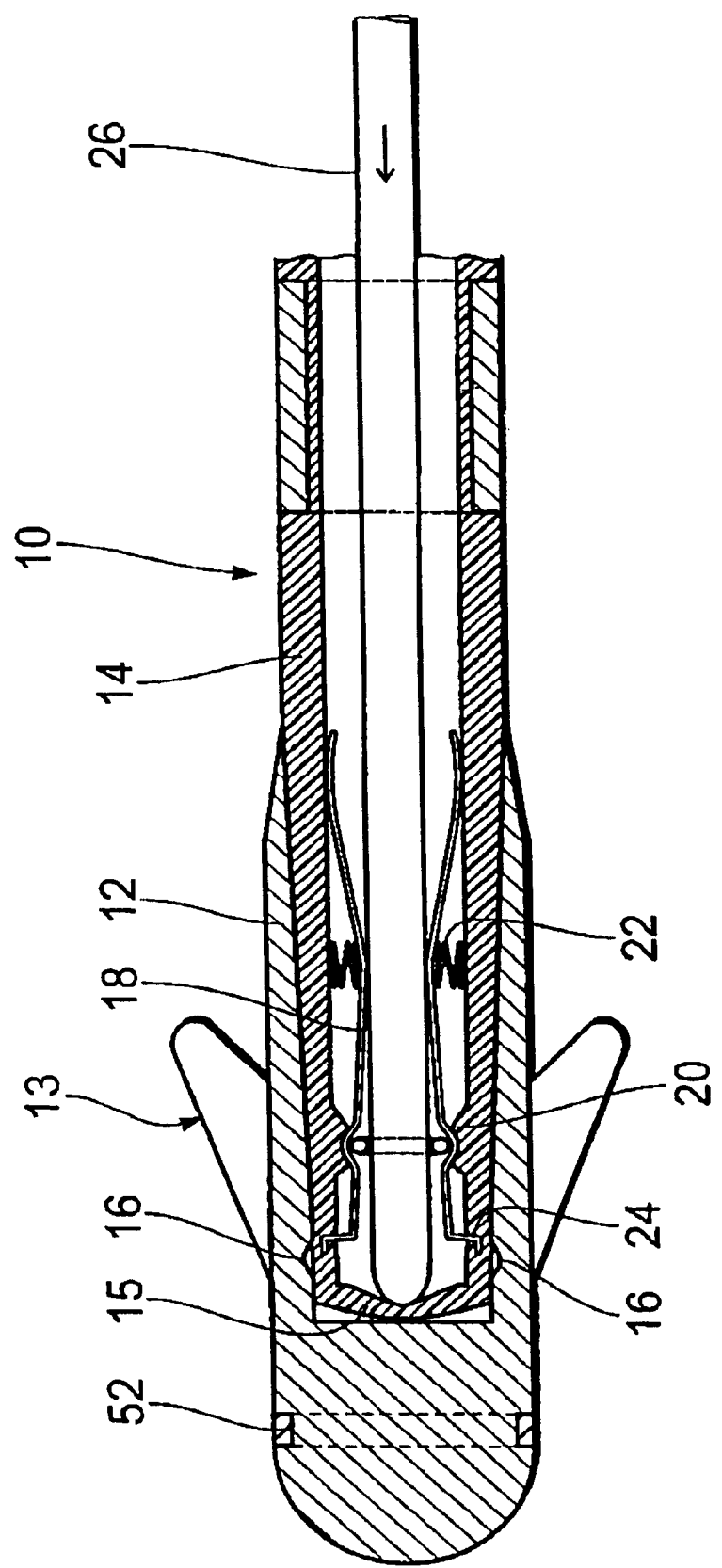

By further inward displacement of the bar 26 in the direction indicated, it reaches the end wall 15 and causes it to bulge outwardly; see FIG. 1c. As a result the fixing means 12 are displaced forwardly with respect to the electrode line 10 and easily released. As the casing 14, where it is surrounded by the fixing means 12, tapers slightly towards its distal end, the electrode line 10 and the fixing means 12 are separated immediately. The taper of the casing 14 is still further increased by virtue of the end wall 15 being caused to bulge outwardly by the bar 26. In that way, the fixing means 12 can be actively separated from the electrode line 10.

An alternative configuration (not shown) of the embodiment illustrated in FIG. 1 does not have any projections on the casing 14 and also does not have any spring bars. The fixing means is held on the casing, which otherwise corresponds to the casing 14, solely by virtue of the fact that this casing does not further taper just before its distal end or even is enlarged again in diameter towards the distal end. A bar like the bar 26 then serves to cause the end wall 15 to bulge outwardly as described, and thereby at the same time to produce a taper at the distal end of the casing 14, which releases the fixing means clamped on the distal end of the casing and thus releases the connection between the casing and the fixing means.

Figure 2:
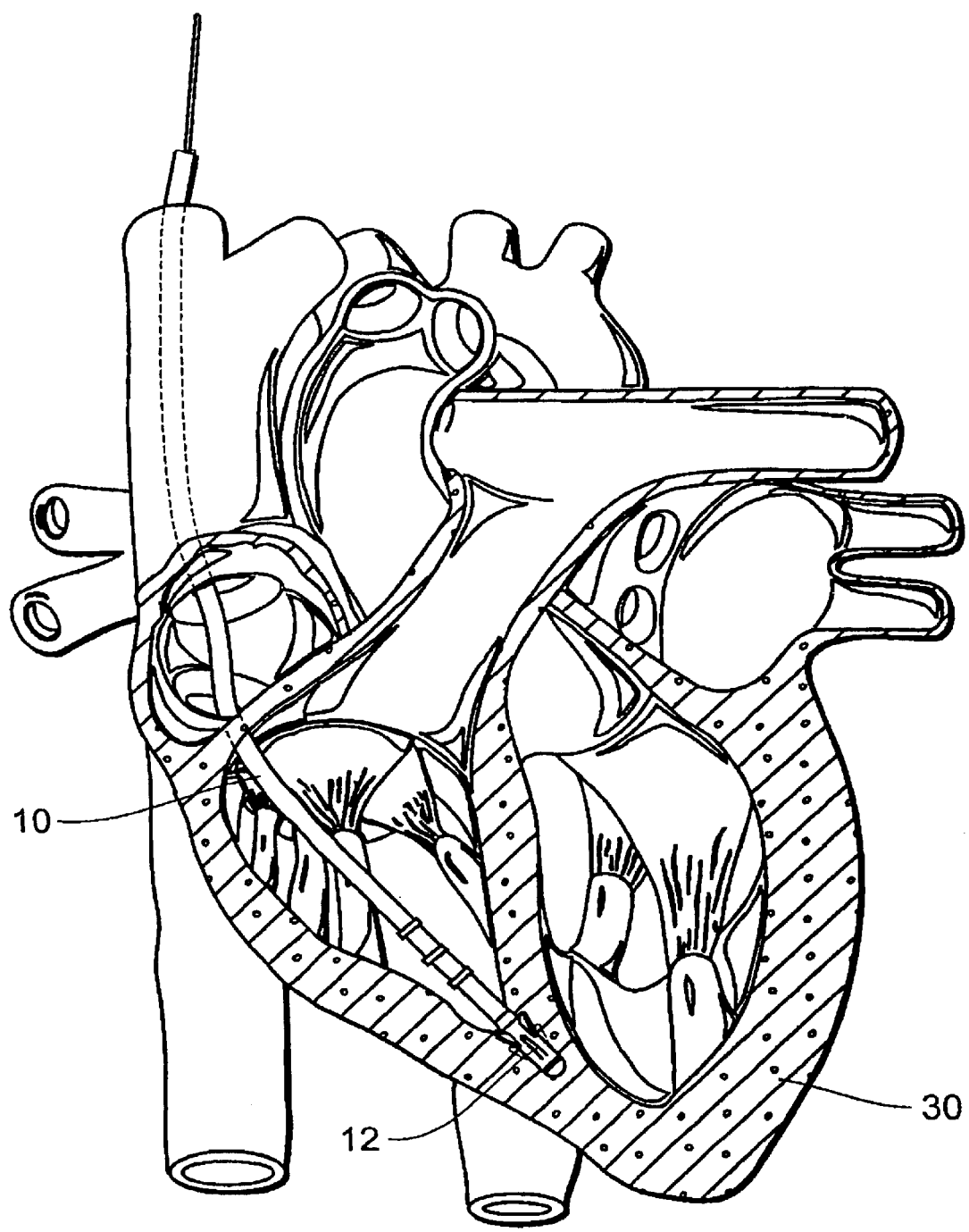
FIG. 2 shows the electrode line of FIG. 1 inserted into and anchored in the ventricle of a human heart.

FIG. 2 shows the electrode line 10 of FIG. 1 with the fixing means 12 thereof anchored in the cardiac tissue or myocardium of a ventricle of a human heart 30. The fixing means 12 grows into the myocardium of the heart 30 as time passes, so that the electrode line 10 cannot be removed without damaging the myocardium. In order to remove the electrode line 10, the coupling between the fixing means 12 and the electrode line 10 is released in the manner described hereinbefore so that the electrode line 10 can be removed without stressing and loading the myocardium and the fixing means 12 in the myocardium. The fixing means 12 can, for example, consist entirely of silicone synthetic resin and are harmless to the heart.

FIG. 3 shows an alternative embodiment of an electrode line 10' with fixing means 12' at the distal end thereof. The fixing means 12' are latched to the rest of the electrode line 10'. That purpose is served by a lip 40' on the fixing means, which engages into a recess 42' in the casing 14' of the electrode line 10'. Connected to the fixing means 12' is a tip electrode 44' which serves to output electrical voltage pulses directly to the myocardium or conversely to receive electrical signals from the myocardium. The tip electrode 44' comprises metal and is contacted by a contact 46' which is connected by way of a coiled electric line 48' to a device for outputting electrical pulses such as for example a defibrillator or a cardiac pacemaker. The contact 46' serves at the same time as an end wall of the casing 14', which seals off the distal end of the electrode line 10'. For that purpose the contact 46' is let with its entire periphery into the casing 14'.

The latching of the fixing means 12' to the rest of the electrode line 10' by means of the lip 40' and the recess 42' is of such a nature that forces to be applied to the fixing means 12' by the myocardium are sufficient to disconnect the connection between the fixing means 12' and the rest of the electrode line 10'. The consequence of this is that the fixing means 12' are released from the rest of the electrode line 10' when the electrode line 10' is pulled out of the ventricle. The fixing means 12' remain together with the tip electrode 44' in the myocardium of the heart 30.

As FIG. 4 shows an electrode line 10" and fixing means 12" can also be of such a configuration that a tip electrode 44" is a fixed component of the electrode line 10" and remains at the distal end of the electrode line 10" when the fixing means 12" are separated from the rest of the electrode line 10".

Further features, which have not been referred to hereinbefore, of the electrode lines 10, 10' and 10" shown in FIGS. 1, 3 and 4 are inter alia ring electrodes 50 which are arranged on the electrode line 10, 10' and 10" for the output of electrical pulses or for receiving electrical signals. In addition, in the region of the connection of the electrode line 10, 10' and 10" to the fixing means 12, 12' and 12", it is possible to provide initially plastic silicone synthetic resin materials which in the manner of a sealing material can seal any gaps which have remained and which in addition by virtue of adhesion forces in relation to the electrode line and the fixing means respectively have an influence on the force with which the fixing means are secured to the electrode line.

All fixing means 12, 12' and 12" have marking means which in the case of the fixing means 12 in FIG. 1 are in the form of a ring and which in FIGS. 3 and 4 are secured to the tines. The marking means 52 contain gold which is body-compatible and opaque in relation to X-rays, that is to say it is visible by means of an X-ray apparatus. In that way the marked fixing means 12, 12' and 12" can be located by means of an X-ray apparatus upon insertion of a new electrode line.

What is claimed is:

1. An electrode arrangement comprising:

an electrode line having an interior and a distal end, wherein the electrode line has closed casing for sealing off the interior of the electrode line and at least one electrically conducting surface region having at least one electrode at the distal end, wherein the electrode line with the electrode has a diameter which is one of a) uniform over its entire length and b) tapering toward the distal end of the electrode line; and means coupled to the electrode line for fixing the distal end of the electrode line in body tissue, said fixing means being adapted to be separated from the electrode line by forces acting axially within the electrode arrangement such that the interior of the electrode line remains sealed during separation; and a synthetic resin material in a separation location between the fixing means and the electrode line, the synthetic resin material being plastic when the fixing means are connected to the electrode line.

2. The electrode arrangement of claim 1, wherein the fixing means are adapted to anchor the electrode arrangement to heart tissue.

3. The electrode arrangement of claim 1, wherein the separation location has a configuration, and wherein the fixing means is coupled to the electrode line at the separation location and is adapted to be separated from the electrode line by defined forces that are predetermined by the configuration of the separation location.

4. The electrode arrangement of claim 3, wherein the fixing means is adapted to be separated by the defined forces which include forces exerted in a longitudinal direction of the electrode line by the body tissue as a result of tensile forces exerted on the electrode line.

5. The electrode arrangement of claim 3, wherein the electrode line has a recess at the separation location, and the fixing means has a projection for engaging the recess.

6. The electrode arrangement of claim 1, wherein the fixing means includes means for marking being locatable by means for locating.

7. The electrode arrangement of claim 6, wherein the means for marking includes gold.

8. The electrode arrangement of claim 6, wherein the fixing means includes barb-shaped tines, and wherein the means for marking are arranged in the tines.

9. The electrode arrangement of claim 1, wherein the diameter of the electrode line is uniform over its entire length.

10. An electrode arrangement comprising:

an electrode line having an interior and a distal end, wherein the electrode line has closed casing for sealing off the interior of the electrode line and at least one electrically conducting surface region having at least one electrode at the distal end, wherein the electrode line with the electrode has a diameter which tapers toward the distal end of the electrode line;

means coupled to the electrode line for fixing the distal end of the electrode line in body tissue, said fixing means being adapted to be separated from the electrode line by forces acting axially within the electrode arrangement such that the interior of the electrode line remains sealed during separation; and a synthetic resin material in a separation location between the fixing means and the electrode line, the synthetic resin material being plastic when the fixing means are connected to the electrode line.

* * * * *